United States Patent [19]

Aya et al.

[11] Patent Number: 4,474,600
[45] Date of Patent: Oct. 2, 1984

[54] HERBICIDALLY ACTIVE NOVEL SUBSTITUTED PHENYLSULFONYLUREA DERIVATIVES

[75] Inventors: Masahiro Aya; Junichi Saito; Kazuomi Yasui, all of Tokyo; Kozo Shiokawa, Kanagawa; Norihisa Morishima, Tokyo; Toshio Goto, Kanagawa, all of Japan

[73] Assignee: Nihon Tokushu Noyaku Seizo K.K., Tokyo, Japan

[21] Appl. No.: 415,629

[22] Filed: Sep. 7, 1982

[30] Foreign Application Priority Data

Sep. 16, 1981 [JP] Japan ................. 56-144590

[51] Int. Cl.³ ............... A01N 9/22; C07Z 239/42; C07D 251/16
[52] U.S. Cl. ............................... 71/92; 71/93; 544/194; 544/211; 544/320; 544/321; 544/328; 544/332; 564/90
[58] Field of Search ............. 544/332, 321, 211; 71/92, 93

[56] References Cited

U.S. PATENT DOCUMENTS

| 4,127,405 | 11/1978 | Levitt | 71/93 |
| 4,169,719 | 10/1979 | Levitt | 71/92 |
| 4,191,553 | 3/1980 | Reap | 544/332 |
| 4,339,267 | 7/1982 | Levitt | 544/330 |
| 4,368,067 | 1/1983 | Budzinski et al. | 71/92 |

FOREIGN PATENT DOCUMENTS

| 1128043 | 7/1982 | Canada | 544/332 |
| 0053038 | 6/1982 | European Pat. Off. | 544/330 |
| 0056969 | 8/1982 | European Pat. Off. | |
| 1468747 | 2/1967 | France | 544/332 |
| 52-122384 | 10/1977 | Japan | |

Primary Examiner—Donald G. Daus
Assistant Examiner—James H. Turnipseed
Attorney, Agent, or Firm—Sprung, Horn, Kramer & Woods

[57] ABSTRACT

Substituted phenylsulfonylurea-derivatives of the general formula

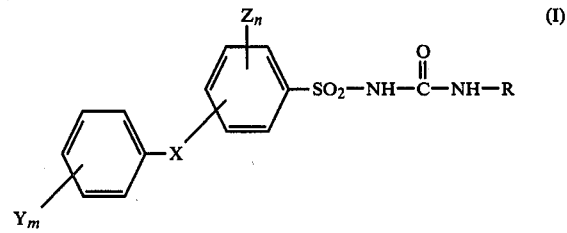

wherein X represents an oxygen atom or a direct bond, Y and Z each represents a halogen atom, a lower alkyl group, a lower alkoxy group or a nitro group, R represents a group:

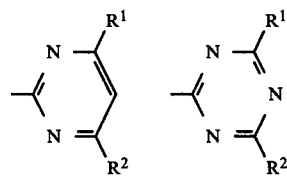

wherein $R^1$ and $R^2$ each represents a lower alkyl group or a lower alkoxy group, m and n each represents 0, 1 or 2 with the proviso that m and n do not represent 0 at the same time, are novel and find use as herbicides. Corresponding substituted benzenesulfonyl isocyanates are novel intermediate compounds for use in preparing compounds of formula (I).

6 Claims, No Drawings

HERBICIDALLY ACTIVE NOVEL SUBSTITUTED PHENYLSULFONYLUREA DERIVATIVES

The present invention relates to certain new substituted phenylsulfonylurea derivatives, to a process for their production and to their use as herbicides, and to certain substituted benzenesulfonyl isocyanates as intermediate products for their production.

It has been disclosed in U.S. Pat. Nos. 4,127,405 and 4,169,719 and in Japanese Published Patent Application No. 52-122384 that compounds of the general formula

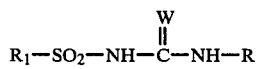

in which
R denotes

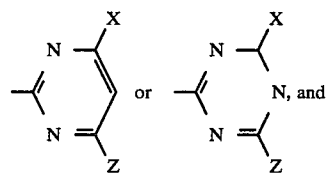

$R^1$ denotes

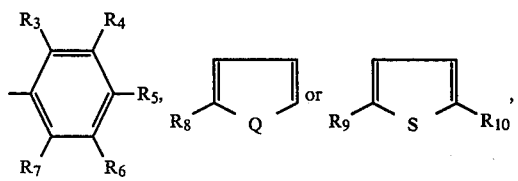

wherein,
R$_3$ and R$_6$ independently denote a hydrogen, fluorine, bromine or iodine atom, an alkyl group of 1 to 4 carbon atoms, an alkoxy group of 1 to 4 carbon atoms, a nitro, trifluoromethyl or cyano group or a CH$_3$S(O)$_n$— or CH$_3$CH$_2$S(O)$_n$— group (in which n is 0, 1 or 2),
R$_4$ denotes a hydrogen, fluorine, chlorine or bromine atom or a methyl group,
R$_5$ denotes a hydrogen, fluorine, chlorine or bromine atom or a methyl or methoxy group,
R$_7$ denotes a hydrogen, fluorine or bromine atom, an alkyl group of 1 or 2 carbon atoms or an alkoxy group of 1 or 2 carbon atoms,
R$_8$, R$_9$ and R$_{10}$ independently denote a hydrogen, chlorine or bromine atom or a methyl group,
W and Q independently denote an oxygen or sulfur atom,
X denotes a hydrogen, chlorine or bromine atom, a methyl or ethyl group, an alkoxy group of 1 to 3 carbon toms, a trifluoromethyl group or CH$_3$S— or CH$_3$OCH$_3$—; and
Z denotes a methyl or methoxy group, with the provisos that (a) where R$_5$ is other than a hydrogen atom, then at least one of R$_3$, R$_4$, R$_6$ and R$_7$ must be other than a hydrogen atom, and at least two of R$_3$, R$_4$, R$_6$ and R$_7$ must be hydrogen atoms; that (b) where R$_5$ is a hydrogen atom and all of R$_3$, R$_4$, R$_6$ and R$_7$ are other than hydrogen atoms, then all of R$_3$, R$_4$, R$_6$ and R$_7$ must be either a chlorine atom or a methyl group; and that (c) where R$_3$ and R$_7$ are both hydrogen atoms, then at least one of R$_3$, R$_4$, R$_5$ and R$_6$ must be a hydrogen atom; and physiologically acceptable salts thereof possess herbicidal activity.

However, the herbicidal properties of these compounds are not always satisfactory from the point of view of the level of action and selectivity.

The present invention now provides, as new compounds, the substituted phenylsulfonylurea derivative of the general formula:

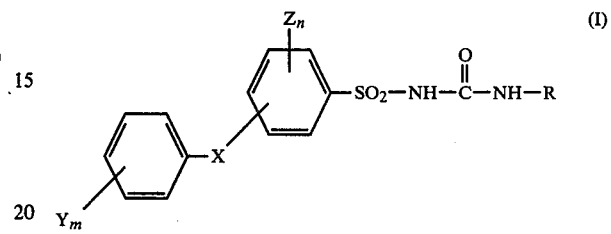

wherein
X represents an oxygen atom or a direct bond,
Y and Z each independently represents a halogen atom, a C$_1$ to C$_6$ alkyl group, a C$_1$ to C$_6$ alkoxy group or a nitro group,
R represents a group of the general formula

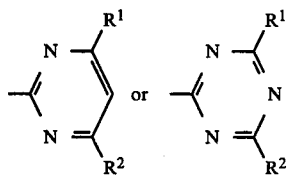

wherein
R$^1$ and R$^2$ each independently represents a C$_1$ to C$_6$ alkyl group or a C$_1$ to C$_6$ alkoxy group and,
m and n are each independently 0, 1 or 2 with the proviso that m and n are not both 0 at the same time.

The present invention further provides a process for the production of a compound of the formula (I) of the present invention characterized in that a compound of the general formula

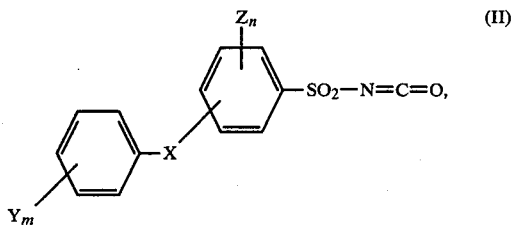

wherein
X, Y, Z, m and n have the meanings given above, is reacted with a compound of the general formula $$H_2N-R \qquad (III)$$

R has the meaning given above.

The present invention also provides, as new compounds, the substituted benzenesulfonyl isocyanates of the general formula:

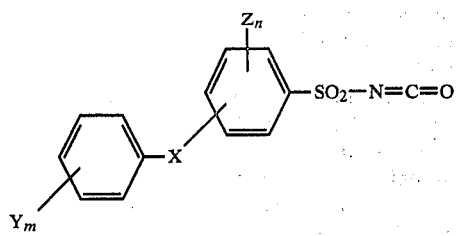

(II)

wherein X, Y, Z, m and n have the meanings given above.

The present invention further provides a process for the production of a compound of formula (II) according to the present invention characterized in that a substituted benzenesulfonamide of the general formula

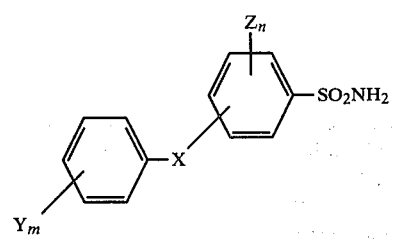

(IV)

wherein X, Y, Z, m and n have the meanings given above, is reacted with phosgene ($COCl_2$) or trichloromethyl chloroformate ($CCl_3OCOCl$) in the presence of a hydrocarbyl isocyanate.

It has now been discovered that the substituted phenylsulfonylurea derivatives of the formula (I) exhibit excellent selective herbicidal activity which could not have been expected from the knowledge of the compounds of the prior art mentioned above. In particular the active compounds of the present invention, as compared with the conventional herbicides which show considerable phytotoxicity to rice plants although showing a herbicidal effect at considerably low dosages, do not show any phytotoxicity to rice plants at all and exhibit an accurate, excellent, selective herbicidal effect at low dosages. The present invention thus represents an enrichment of the art.

Preferred compounds of formula (I) according to the present invention are those in which X represents an oxygen atom or a direct bond, Y and Z each independently represents a fluorine, chlorine, bromine or iodine atom or a methyl, ethyl, propyl, isopropyl, n-(iso-, sec-or tert.-)butyl, methoxy, ethoxy, propoxy, isopropoxy, n-(iso-, sec- or tert.-)butoxy or nitro group, R represents a 2-pyrimidinyl group or 1,3,5-triazin-2-yl group in which 4 and 6 positions of the pyrimidinyl ring or 1,3,5-triazine ring are substituted by a substituent selected from methyl, ethyl, propyl, isopropyl, n-(iso-, sec- or tert.-)butyl, methoxy, ethoxy, propoxy, isopropoxy and n-(iso-, sec- or tert.-)butoxy, and m and n are each independently 0, 1 or 2 with the proviso that m and n do not represent 0 at the same time.

The process according to the present invention for the production of compounds of formula (I) is indicated by the following equation:

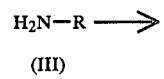

(II)

$H_2N-R \longrightarrow$ (III)

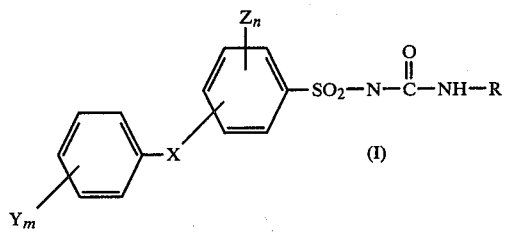

(I)

in which X, Y, Z, R, m and n are as defined above.

Preferred starting materials of formula (II) are those in which X, Y, Z, m and n have the meanings given in the definition of preferred compounds of formula (I) according to the present invention.

Examples of the compounds of the formula (II) which may be mentioned include:

2-(2-chlorophenoxy)benzenesulfonyl isocyanate,
2-(4-chlorophenoxy)benzenesulfonyl isocyanate,
2-methoxy-5-phenylbenzenesulfonyl isocyanate,
2-(4-nitrophenyl)benzenesulfonyl isocyanate,
2-bromo-4-nitro-6-phenylbenzenesulfonyl isocyanate,
2-(2-fluorophenoxy)benzenesulfonyl isocyanate,
2-chloro-6-phenoxybenzenesulfonyl isocyanate,
2-(o-tolyloxy)benzenesulfonyl isocyanate,
5-methyl-2-phenoxybenzenesulfonyl isocyanate,
2-ethoxy-5-phenylbenzenesulfonyl isocyanate,
2-(4-isopropylphenoxy)benzenesulfonyl isocyanate,
2-chloro-6-phenylbenzenesulfonyl isocyanate,
2-(2-methoxyphenoxy)benzenesulfonyl isocyanate and
2-(2,4-dichlorophenoxy)benzenesulfonyl isocyanate.

Preferred starting materials of formula (III) are those in which R has the meaning given in the definition of preferred compounds of formula (I) according to the present invention.

Examples of compounds of the formula (III) which may be mentioned include:

2-amino-4-methoxy-6-methylpyrimidine,
2-amino-4,6-dimethoxy-1,3,5-triazine,
2-amino-4-methoxy-6-methyl-1,3,5-triazine,
2-amino-4,6-dimethoxypyrimidine,
2-amino-4,6-dimethylpyrimidine,
2-amino-4,6-dimethyl-1,3,5-triazine,
2-amino-4,6-diethoxy-1,3,5-triazine,
2-amino-4,6-dipropylpyrimidine, and
2-amino-4-methyl-6-propoxy-1,3,5-triazine.

If, for example 2-(2-chlorophenoxy)benzenesulfonyl isocyanate and 2-amino-4-methoxy-6-methyl pyrimidine are used as starting materials, the process according to the present invention for the production of compounds of formula (I) is illustrated by the following equation:

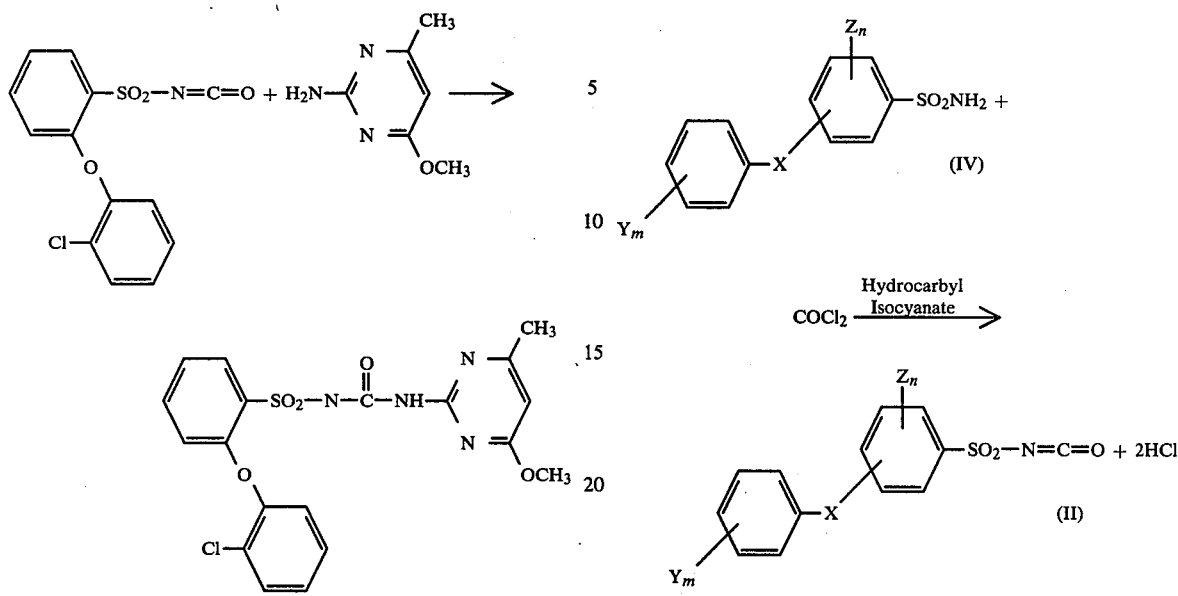

The process for the preparation of the compounds of the formula (I) above according to the present invention is preferably carried out in the presence of a solvent or a diluent. For this purpose, any of the inert organic solvents or diluents may be employed. These include in particular aliphatic, alicyclic and aromatic, optionally chlorinated, hydrocarbons (such as hexane, cyclohexane, petroleum ether, ligroin, benzene, toluene, xylene, methyl chloride, chloroform, carbon tetrachloride, ethylene chloride, trichloroethylene and chlorobenzene), ethers (such as diethyl ether, methyl ether, di-isopropyl ether, dibutyl ether, propylene oxide, dioxane and tetrahydrofuran), ketones (such as acetone, methyl ethyl ketone, methyl isopropyl ketone and methyl isobutyl ketone), nitriles (such as acetonitrile, propionitrile and acylonitrile), esters (such as ethyl acetone and amyl acetate), acid amides (such as dimethylformamide, dimethylacetamide), sulfones and sulfoxides (such as dimethylsulfoxide), sulfolane and bases (such as pyridine).

This process is appropriately carried out in the presence of a catalyst, such as 1,4-diazabicyclo[2,2,2]octane.

The reaction temperature can be varied within a substantial range. In general, the reaction is carried out at a temperature between $-20°$ C. and the boiling point of the reaction mixture, preferably between $0°$ and $100°$ C.

The process according to the invention is preferably carried out under ambient pressure, although it can be carried out under elevated or reduced pressure.

As mentioned previously, the substituted benzenesulfonyl isocyanates of the formula (II) above are novel compounds which form a further subject of the present invention and are useful as intermediates to the substituted phenylsulfonylurea derivatives of the formula (I) above which, as described above, have excellent selective herbicidal activity.

The further process according to the present invention for the production of starting compounds of formula (II) is indicated by the following equation:

wherein X, Y, Z, m and n are as defined above.

In the above reaction scheme, trichloromethyl chloroformate ($CCl_3OCOCl$) may be reacted in place of phosgene ($COCl_2$).

Specific examples of the substituted benzenesulfonamide of the formula (IV) which is a starting material for the preparation of a substituted benzenesulfonyl isocyanate of the formula (II) include:

2-(2-chlorophenoxy)benzenesulfonamide,
2-(4-chlorophenoxy)benzenesulfonamide,
2-methoxy-5-phenylbenzenesulfonamide,
2-(4-nitrophenyl)benzenesulfonamide,
2-bromo-4-nitro-6-phenylbenzenesulfonamide,
2-(2-fluorophenoxy)benzenesulfonamide,
2-chloro-6-phenoxybenzenesulfonamide,
2-(o-tolyloxy)benzenesulfonamide,
5-methyl-2-phenoxybenzenesulfonamide,
2-ethoxy-5-phenylbenzenesulfonamide,
2-(4-isopropylphenoxy)benzenesulfonamide,
2-chloro-6-phenylbenzenesulfonamide,
2-(2-methoxyphenoxy)benzenesulfonamide, and
2-(2,4-dichlorophenoxy)benzenesulfonamide.

The reaction for the preparation of the compounds of formula (II) is carried out in the presence of a hydrocarbyl isocyanate, which hydrocarbyl radical may be an alkyl group of 3 to 8 carbon atoms or a cycloalkyl group of 5 to 8 carbon atoms. Specific examples of suitable hydrocarbyl isocyanates include:

n-butyl isocyanate,
n-hexyl isocyanate, and
cyclohexyl isocyanate.

If, for example, 2-(2-chlorophenoxy)benzenesulfonamide, trichloromethyl chloroformate and n-butyl isocyanate are used as reactants, the process according to the invention for the preparation of compounds of formula (II) is illustrated by the following equation:

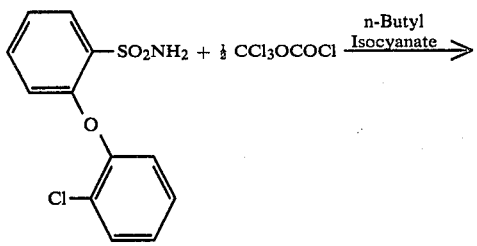

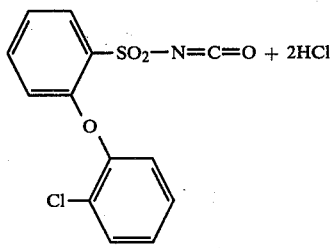

The hydrocarbyl isocyanate, which is an essential reactant for the production of compounds of formula (II), can be recovered at the end of the reaction, and therefore this process is industrially advantageous.

The process for the production of compounds of formula (II) may be carried out in any of those inert organic solvents or diluents mentioned previously as diluents in the production of compounds of formula (I).

Further, the process for the production of compounds of formula (II) is appropriately carried out in the presence of a catalyst, such as tertiary amines (for example triethylamine, dimethylcyclohexylamine and 1,4-diazabicyclo[2,2,2]octane).

The reaction temperature can be varied within a substantial range. In general, the reaction is carried out at a temperature between −20° C. and the boiling point of the reaction mixture, preferably between 80° and 150° C.

This process according to the invention is preferably carried out under ambient pressure, although it can be carried out under elevated or reduced pressure.

Since the compounds of formula (I) according to the present invention exhibit no or a low toxicity to warm blooded animals, the said compounds are very useful for weed control.

By "weeds" in the broadest sense there are meant plants growing to places where they are not desired.

The active compounds according to the present invention are excellent with regard to their safety, manifest a superior herbicidal activity and have wide herbicidal spectra.

The active compounds according to the present invention may be used, for example, to combat the following plants:

dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver, Centaurea and Solanum; and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monocharia, Fimbristylis, Sagittaria, Eleocharis, Scirpus, Paspalum, Ischaemum, Spenoclea, Dactyloctenium, Agrostis, Alopecurus and Apera.

The active compounds according to the present invention may be used, for example, as selective herbicides in the following cultures:

dicotyledon cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita; and monocotyledon cultures of the genera Oryza, Zea, Triticum, Hordeum, Avena, Secale, Sorghum, Panicum, Saccharum, Ananas, Asparagus and Allium.

However, the use of the active compounds according to the invention is in no way restricted to these genera but also embraces other plants, in the same way.

Depending on the concentrations, the compounds can be used for the total combating of weeds, for example on industrial terrain and railway tracks and on paths and squares with or without trees. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cacao plantations, soft fruit plantings and hopfields, and for the selective combating of weeds in annual cultures.

The active compounds according to the present invention show a superior selective control effect, especially when they are employed as pre-germination soil treating agents or as plant stems-, leaves- and soil-treating agents for weeds in paddy rice fields. For example they show herbicidal activity on weeds in paddy rice fields such as those listed below without showing any harmful effect on rice plants:

the dicotyledon weeds *Rotala indica* Koehne, *Lindernia procumbens* Philcox, *Ludwigia prostrata* Roxburgh, *Potamogeton distinctus* A. Benn and *Elatine triandra* Schk; and the monocotyledon weeds *Echinochloa crus-galli* beauv. var., *Monochloria vaginalis* Presl., *Eleocharis acicularis* L., *Eleocharis Kuroguwai* Ohwi, *Cyperus difformis* L. *Cyprus serotinus* Rottboel, *Sagittaria pygmaea* Miq., *Alisma canaliculatum* A. Br. et Bouché and *Scirpus juncoides* Roxburgh var.

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulfoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hyrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs and trace nutrients, such as salts or iron, manganese, boron, copper, cobalt, molybdenum and zinc.

The formulations in general contain from 0.001 to 100% by weight of active compound, preferably from 0.05 to 95% by weight.

The active compounds according to the invention can be present in the formulations, or in the various use forms, as compounds, such as fungicides, bactericides, insecticides, nematicides, herbicides, bird repellents, growth factors, plant nutrients and agents for improving soil structure.

Particularly, by adding appropriate amounts of other active ingredients to the active compounds according to this invention, a wider herbicidal spectrum and more accurate control effect can be obtained, and a synergistic effect by mixing thereof can also be obtained. Examples of such other active ingredients are as follows:

2-chloro-2', 6'-diethyl-N-(butoxymethyl)-acetanilide, N-(O,O-dipropyl-diethylphosphorylacetyl)2-methyl-piperidine, S-(4-chlorobenzyl)-N,N-diethylthiol carbamate, S-ethyl-N,N-hexamethylenethiol carbamate, O-methyl-O-(2-nitro-p-tolyl)-N-isopropylphosphoramidothioate, O-ethyl-O-(2-nitro-5-methylphenyl)-N-sec-butylphosphoramidothioate, 3,4-dimethyl-2,6-dinitro-N-1-ethylpropylaniline, α,α,α-trifluoro-2,6-dinitro-N,N-dipropyl-p-toluidine, 2-chloro-2',6'-diethyl-N-(n-propoxyethyl) acetanilide, 4,5-dichloro-1,3-thiazol-2-yloxyacetic acid N-isopropyl-N-ethoxyethoxyamide, 5-ethyl-1,3,4-thiadiazol-2-yloxyacetic acid 1',2',3',4'-tetrahydroquinolide, benzothiazol-2-yloxyacetic acid N,N-diallylamide, benzoxazol-2-yloxyacetic acid N-sec-butyl-N-methylamide, benzoxazol-2-yloxyacetic acid N-cyclohexyl-N-methylamide, benzothiazol-2-oxyacetic acid N-methyl-N-(1-methylpropargyl)amide, benzoxazol-2-yloxyacetic acid N-benzyl-N-propargylamide, benzothiazol-2-yloxyacetic acid 2'-ethylpiperidide, benzothiazol-2-yloxyacetic acid 2',4'-dimethylpiperidide, benzoxazol-2-yloxy acetic acid 2',4',6'-trimethylpiperidide, benzoxazol-2-yloxyacetic acid hexamethyleneimide, benzothiazol-2-yloxyacetic acid perhydroindolide, benzoxazol-2-yloxyacetic acid perhydroindolide, benzothiazol-2-yloxyacetic acid 1',2',3',4'-tetrahydroquinolide, benzoxazol-2-yloxyacetic acid 2'-methyl-1',2',3',4'-tetrahydroquinolide, benzoxazol-2-yloxyacetic acid N-methylanilide, benzothiazol-2-yloxyacetic acid N-methylanilide, benzoxazol-2-yloxyacetic acid N-ethylanilide, benzoxazol-2-ylacetic acid N-propylanilide, benzoxazol-2-yloxyacetic acid N-isopropylanilide, benzothiazol-2-yloxyacetic acid N-methyl-N-2'methoxyanilide, benzoxazol-2-yloxyacetic acid N-methyl-N-2'-methoxyanilide, benzoxazol-2-yloxyacetic acid N-methyl-N-2'-trifluoromethylanilide, benzothiazol-2-yloxyacetic acid N-methyl-N-2'-chloroanilide, benzoxazol-2-yloxyacetic acid N-methyl-N-2'-chloroanilide, benzothiazol-2-yloxyacetic acid N-methyl-N-2'-fluoroanilide, benzoxazol-2-yloxyacetic acid N-methyl-N-2'-fluoroanilide, benzothiazol-2-yloxyacetic acid N-methyl-N-3'-methylanilide, benzoxazol-2-yloxyacetic acid N-methyl-N-3'-methylanilide, benzothiazol-2-yloxyacetic acid N-methyl N-3'-methoxyanilide, benzoxazol-2-yloxyacetic acid N-methyl-N-3'-methoxyanilide, benzothiazol-2-yloxyacetic acid N-methyl-N-3'-isopropylanilide, benzoxazol-2-yloxyacetic acid N-methyl-N-3'-isopropoxyanilide, benzothiazol-2-yloxyacetic acid N-methyl-3'-trifluoromethylanilide, benzoxazol-2-yloxyacetic acid N-methyl-N-3'-trifluoromethylanilide, benzothiazol-2-yloxyacetic acid N-methyl-N-3'-chloroanilide, benzoxazol-2-ylacetic acid N-methyl-N-3'-chloroanilide, benzothiazol-2-yloxyacetic acid N-methyl-N-3'-fluoroanilide, benzoxazol-2-yloxyacetic acid N-methyl-N-3'-fluoroanilide, benzothiazol-2-yloxyacetic acid N-methyl-3'-bromoanilide, benzoxazol-2-yloxyacetic acid N-methyl-3'-bromoanilide, benzothiazol-2-yloxyacetic acid N-methyl-N-3'-methylanilide, benzoxazol-2-yloxyacetic acid N-methyl-N-4'-methoxyanilide, benzoxazol-2-yloxyacetic acid N-methyl-N-4'-fluoroanilide, benzoxazol-2-yloxyacetic acid N-methyl-N-2',3'-dimethylanilide, benzoxazol-2-yloxyacetic acid N-methyl-N-2',3'-dichloroanilide, benzoxazol-2-yloxyacetic acid N-methyl-N-4'-chloro-2'-methylanilide, benzoxazol-2-yloxyacetic acid N-methyl-N-2',5'-dichloroanilide, benzoxazol-2-yloxyacetic acid N-methyl-N-2',5'-dichloroanilide, benzothiazol-2-yloxyacetic acid N-methyl-N-3',5'-dimethylanilide, benzoxazol-2-yloxyacetic acid N-methyl-N-3',5'-dimethylanilide, benzoxazol-2-yloxyacetic acid N-methyl-N-3',5'-di-trifluoromethylanilide, benzoxazol-2-yloxyacetic acid N-methyl-N-5'-indanylamide, benzothiazol-2-yloxyacetic acid N-methyl-N-3'-ethylanilide, benzoxazol-2-yloxyacetic acid N-methyl-N-3'-ethylanilide and benzothiazol-2-yloxyacetic acid N-isopropylanilide.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, scattering or dusting.

The active compounds according to the invention can be applied either before or after emergence of the plants. They are preferably applied before emergence of the plants, that is to say by the pre-emergence method. They can also be incorporated into the soil before sowing.

Further, it is also possible to apply the active compounds by means of the ultra-low-volume method, whereby it is possible to employ the compounds at a concentration of up to 100% by weight.

In actual use, the content of the active ingredients in the various preparations and ready-to-use preparations is generally in the range of 0.01 to 95% by weight, preferably 0.05 to 60% by weight.

The dosage of the active compound per unit area is generally 0.1 to 3 kg, preferably 0.2 to 1 kg, per hectare. In special cases, however, it is possible, or sometimes even necessary, to employ a dosage higher or lower than the above range.

The present invention also provides herbicidal composition containing as active ingredient a compound of the present invention in admixture with a solid or liquefied gaseous diluent or carrier or in admixture with a liquid diluent or carrier containing a surface-active agent.

The present invention also provides a method of combating weeds which comprises applying to the weeds or to a habitat thereof, a compound of the present invention alone or in the form of a composition containing as active ingredient a compound of the present invention in admixture with a diluent or carrier.

The present invention further provides crops protected from damage by weeds by being grown in areas in which immediately prior to and/or during the time of the growing a compound of the present invention was applied alone or in admixture with a diluent or carrier.

It will be seen that the usual methods of providing a harvested crop may be improved by the present invention.

The following examples illustrate the production of starting compounds of formula (II) and of compounds of formula (I).

Preparation of starting materials

EXAMPLE 1

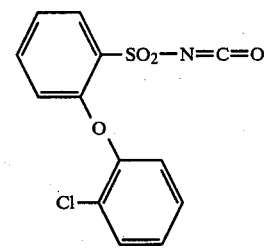

(IIa)

11.4 g of 2-(2-chlorophenoxy)benzenesulfonamide, 4 g of n-butyl isocyanate and 0.5 g of 1,4-diazabicyclo[2,2,2]octane were added to 50 ml of xylene, and the mixture was heated at reflux with stirring for 2 hours. Thereafter, the internal temperature was reduced to 125° C., and a solution of 6 g of trichloromethyl chloroformate in 15 ml of xylene was added dropwise to the above solution at 120° to 125° C. for 2 hours. After the addition, the solution was heated for 2 hours. The solution was cooled, the insoluble compounds were filtered off, the solvent was distilled off, and the contents were distilled to obtain 9.3 g of the desired product, 2-(2-chlorophenoxy)benzenesulfonyl isocyanate, b.p. 145° to 148° C./0.5 mmHg.

Further substituted benzenesulfonyl isocyanates of the formula (II) according to this invention as indicated in following Table 1 were prepared as described using the indicated starting materials.

TABLE 1

| Intermediate II | Starting Material | Starting Material | Product |
|---|---|---|---|
| b | 2-(4-Chlorophenoxy)benzenesulfonamide | Trichloromethyl chloroformate | 2-(4-Chlorophenoxy)benzenesulfonyl isocyanate |
| c | 2-(2-Fluorophenoxy)benzenesulfonamide | Phosgene | 2-(2-Fluorophenoxy)benzenesulfonyl isocyanate |
| d | 2-Chloro-6-phenoxybenzenesulfonamide | Trichloromethyl chloroformate | 2-Chloro-6-phenoxybenzenesulfonyl isocyanate |
| e | 2-Chloro-6-phenylbenzenesulfonamide | Trichloromethyl chloroformate | 2-Chloro-6-phenylbenzenesulfonyl isocyanate |
| f | 2-Methoxy-5-phenylbenzenesulfonamide | Phosgene | 2-Methoxy-5-phenylbenzenesulfonyl isocyanate |
| g | 2-Ethoxy-5-phenylbenzenesulfonamide | Phosgene | 2-Ethoxy-5-phenylbenzenesulfonyl isocyanate |
| h | 2-(2-Methoxyphenoxy)benzenesulfonamide | Phosgene | 2-(2-Methoxyphenoxy)benzenesulfonyl isocyanate |
| i | 2-(4-Nitrophenyl)benzenesulfonamide | Trichloromethyl chloroformate | 2-(4-Nitrophenyl)benzenesulfonyl isocyanate |
| j | 2-(o-Tolyoxy)benzenesulfonamide | Phosgene | 2-(o-Tolyoxy)benzenesulfonyl isocyanate |
| k | 5-Methyl-2-phenoxybenzenesulfonamide | Phosgene | 5-Methyl-2-phenoxybenzenesulfonyl isocyanate |
| l | 2-(4-Isopropylphenoxy)-benzenesulfonamide | Trichloromethyl chloroformate | 2-(4-Isopropylphenoxy)benzenesulfonyl isocyanate |
| m | 2-Bromo-4-nitro-6-phenyl-benzeneamide | Trichloromethyl chloroformate | 2-Bromo-4-nitro-6-phenylbenzenesulfonyl isocyanate |
| n | 2-(2,4-Dichlorophenoxy)-benzenesulfonamide | Phosgene | 2-(2,4-Dichlorophenoxy)benzenesulfonyl isocyanate |

Preparative Example
EXAMPLE 2

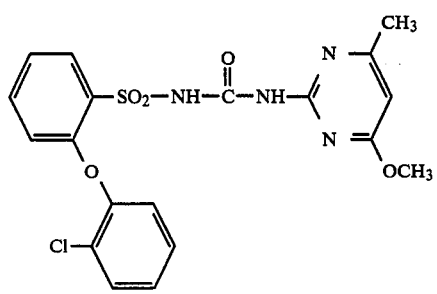
(1)

3.1 g of 2-(2-chlorophenoxy)benzenesulfonyl isocyanate was dissolved in 13 ml of xylene. This solution was added dropwise to a suspension of 1.39 g of 2-amino-4-methoxy-6-methylpyrimidine in 13 ml of acetonitrile with stirring. After the addition, this solution was heated at reflux for an hour, and allowed to stand at room temperature overnight. The formed crystals were filtered out to obtain 4.3 g of the desired product, N-2-(2-chlorophenoxy)phenylsulfonyl, N'-(4-methoxy-6-methyl-2-pyrimidyl)urea, m.p. 216° to 220° C.

The compounds indicated in following Table 2 were prepared as described using appropriate corresponding starting materials.

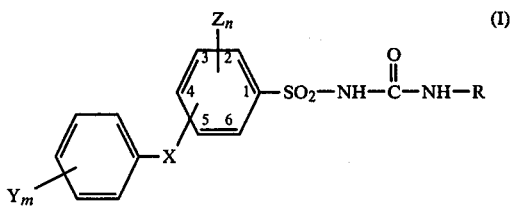
(I)

TABLE 2

| Compound No. | $Y_m$-〈〉-X | n | Z | R | Melting point (°C.) |
|---|---|---|---|---|---|
| 2 | 2-O-〈〉-Cl (ortho) | 0 | — | pyrimidyl with OCH3, OCH3 | 201–204 |
| 3 | 2-O-〈〉-Cl (para) | 0 | — | pyrimidyl with CH3, OCH3 | 213–215 |
| 4 | 2-O-〈〉-Cl (para) | 0 | — | pyrimidyl with CH3, OCH3 | 157–160 |
| 5 | 2-O-〈〉-Cl (para) | 0 | — | pyrimidyl with OCH3, OCH3 | 155–158 |
| 6 | 5-〈〉 | 1 | 2-OCH3 | pyrimidyl with OCH3, OCH3 | 217–220 |

TABLE 2-continued

| Compound No. | Y_m—⌬—X | n | Z | R | Melting point (°C.) |
|---|---|---|---|---|---|
| 7 | 5-phenyl | 1 | 2-OCH$_3$ | triazine with CH$_3$, N, OCH$_3$ | 203–205 |
| 8 | 5-phenyl | 1 | 2-OCH$_3$ | triazine with OCH$_3$, N, OCH$_3$ | 151–152 |
| 9 | 2-(4-NO$_2$)phenyl | 0 | — | triazine with CH$_3$, N, CH$_3$ | 203–204 |
| 10 | 2-(4-NO$_2$)phenyl | 0 | — | triazine with CH$_3$, N, OCH$_3$ | 207–210 |
| 11 | 2-(4-NO$_2$)phenyl | 0 | — | triazine with CH$_3$, N, OCH$_3$ | 181–185 |
| 12 | 2-(4-NO$_2$)phenyl | 0 | — | triazine with OCH$_3$, N, OCH$_3$ | 175–177 |
| 13 | 2-phenyl | 2 | 4-NO$_2$ 6-Br | triazine with CH$_3$, N, OCH$_3$ | 146–149 |
| 14 | 2-phenyl | 2 | 4-NO$_2$ 6-Br | triazine with CH$_3$, N, OCH$_3$ | 137–140 |

TABLE 2-continued

| Compound No. | $Y_m$ (structure with X) | n | Z | R | Melting point (°C.) |
|---|---|---|---|---|---|
| 15 | 2- (phenyl) | 2 | 4-NO₂ 6-Br | triazine with two OCH₃ groups | 168-170 |

The compounds indicated in the following Table 3 were prepared as described using the indicated starting materials.

TABLE 3

| Compound No. | Starting Material | Starting Material | Product |
|---|---|---|---|
| 16 | 2-(2-Chlorophenoxy)-benzenesulfonyl isocyanate | 2-Amino-4-methoxy-6-methyl-1,3,5-triazine | N—[2-(2-Chlorophenoxy)phenylsulfonyl], N'—(4-methoxy-6-methyl-1,3,5-triazin-2-yl)urea |
| 17 | 2-(2-Chlorophenoxy)-benzenesulfonyl isocyanate | 2-Amino-4,6-dimethoxy-pyrimidine | N—[2-(2-Chlorophenoxy)phenylsulfonyl], N'—(4,6-dimethoxy-2-pyrimidyl)urea |
| 18 | 2-(2-Fluorophenoxy)-benzenesulfonyl | 2-Amino-4,6-dimethoxy-1,3,5-triazine | N—[2-(2-Fluorophenoxy)phenylsulfonyl], N'—(4,6-dimethoxy-1,3,5-triazin-2-yl)urea |
| 19 | 2-(2-Fluorophenoxy)-benzenesulfonyl | 2-Amino-4-methoxy-6-methyl-1,3,5-triazine | N—[2-(2-Fluorophenoxy)phenylsulfonyl], N'—(4-methoxy-6-methyl-1,3,5-triazin-2-yl)urea |
| 20 | 2-Chloro-6-phenoxy-benzenesulfonyl isocyanate | 2-Amino-4-methoxy-6-methyl-1,3,5-triazine | N—2-Chloro-6-phenoxyphenylsulfonyl, N'—(4-methoxy-6-methyl-1,3,5-triazine-2-yl)urea |
| 21 | 2-Chloro-6-phenoxy-benzenesulfonyl isocyanate | 2-Amino-4,6-dimethyl-pyrimidine | N—2-Chloro-6-phenoxyphenylsulfonyl, N'—(4,6-dimethyl-2-pyrimidyl)urea |
| 22 | 2-Chloro-6-phenyl-benzenesulfonyl isocyanate | 2-Amino-4,6-dimethoxy-1,3,5-triazine | N—(3-Chloro-2-biphenylsulfonyl), N'—(4,6-dimethoxy-1,3,5-triazin-2-yl)urea |
| 23 | 2-Chloro-6-phenyl-benzenesulfonyl isocyanate | 2-Amino-4-methoxy-6-methyl-1,3,5-triazine | N—(3-Chloro-2-biphenylsulfonyl), N'—(4-methoxy-6-methyl-1,3,5-triazine-2-yl)urea |
| 24 | 5-Methyl-2-phenoxy-benzenesulfonyl isocyanate | 2-Amino-4,6-dimethoxy-1,3,5-triazine | N—(5-Methyl-2-phenoxyphenylsulfonyl), N'—(4,6-dimethoxy-1,3,5-triazine-2-yl)urea |
| 25 | 2-(2-Methoxyphenoxy)-benzenesulfonyl isocyanate | 2-Amino-4-methoxy-6-methylpyrimidine | N—[2-(2-Methoxyphenoxy)phenylsulfonyl], N'—(4-methoxy-6-methyl-2-pyrimidyl)urea |
| 26 | 2-(2,4-Dichlorophenoxy)-benzenesulfonyl isocyanate | 2-Amino-4-methoxy-6-methyl-1,3,5-triazine | N[2-(2,4-Dichlorophenoxy)phenylsulfonyl]N'—(4-methoxy-6-methyl-1,3,5-triazin-2-yl)-urea |

Compositions according to the invention are illustrated in the following examples. In these examples, the compounds according to the invention are each identified by the number (given in brackets) from Example 2 and Tables 2 and 3.

EXAMPLE 3

15 Parts by weight of compound (1), 80 parts by weight of a 1:5 mixture of powder diatomaceous earth and powdered clay, 2 parts by weight of sodium alkylbenzenesulfonate and 3 parts by weight of a condensate of sodium alkylnaphthalenesulfonate and formalin were ground and mixed to prepare a wettable powder. It was diluted with water before spraying.

EXAMPLE 4

10 Parts by weight of compound (2), 75 parts by weight of dimethylformamide, 8 parts by weight of polyoxyethylene alkylphenyl ether and 7 parts by weight of calcium alkylbenzenesulfonate were mixed and stirred to prepare an emulsion. It was diluted with water before spraying.

EXAMPLE 5

2 Parts by weight of compound (3) and 98 parts by weight of powder clay were ground and mixed to prepare a dusting agent.

EXAMPLE 6

1.5 Parts by weight of compound (4), 0.5 part by weight of isopropyl hydrogenphosphate (PAP) and 0.5 part by weight of powdered clay were ground and mixed to prepare a dusting agent.

EXAMPLE 7

10 Parts by weight of compound (5), 30 parts by weight of bentonite (montmorillonite), 58 parts by weight of talc and 2 parts by weight of lignin sulfonate were mixed, and 25 parts by weight of water was added to and intimately mixed with the mixture. The resulting mixture was pelletized into granules of 10 to 40 mesh through an extruding granulator, and dried at 40° to 50° C. to prepare granules. They were applied by scattering.

EXAMPLE 8

95 Parts by weight of clay mineral particles having a particle size distribution of 0.2 to 2 mm were charged into a rotary mixer, uniformly wetted with 5 parts by weight of compound (6) by spraying with a solution of compound (6) dissolved in an organic solvent, and dried at 40° to 50° C. to prepare granules. They were applied by scattering.

The herbicidal activity of the compounds of this invention is illustrated by the following biotest example.

In this example, the compounds according to the present invention are each identified by the number (given in brackets) from Example 2 and Tables 2 and 3.

The known comparison compound is identified as follows:

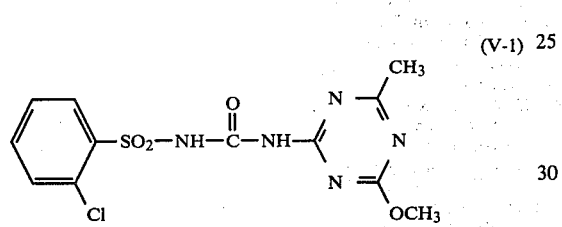

(V-1)

N-2-Chlorophenylsulfonyl-N'-(4-methoxy-6-methyl-1,3,5-triazin-2-yl)urea (a compound described in Japanese Published Patent Application No. 52-122384).

EXAMPLE 9

Plant Stems-, Leaves- and Soil-Treating Test on Weeds in Paddy Rice Fields under Full Water Conditions (Pot Test)

Solvent: 5 parts by weight of acetone
Emulsifier: 1 part by weight of benzyloxypolyglycol ether To produce a suitable preparation of active compound, 1 part by weight of the active compound was mixed with the stated amount of solvent, the stated amount of emulsifier was added and the concentrate was diluted with water to the desired concentration.

Paddy rice field soil was filled in 1/5,000 are Wagner pots and paddy rice seedlings (brandname: "Kinmaze") at the 2 to 3 leaf stage (about 10 cm in plant height) were transplanted, 2 seedlings per pot. Then, seeds of *Echinochloa crus-galli* Beauv. var., *Cyperus iria* L., *Monochoria vaginalis* Presl, *Scirpus juncoides* Roxburgh var. and broadleaf weeds, frangments of *Eleocharis acicularis* L. and roots of *Cyperus serotinus* Rottboel and *Sagittaria pygmaea* Miq. were inoculated and wet conditions were maintained. After *Echinochloa crus-galli* Beauv. var. had been grown to about the 2-leaf stage (7 to 9 days after inoculation), water was filled to about 6 cm in depth and a predetermined amount of each of the compounds according to this invention in the form of an emulsion was applied to water by pipetting. Water was leaked by 2 to 3 cm in depth per day for two days after treatment, and thereafter full water conditions of about 3 cm in depth were maintained. Four weeks after chemical treatment, the herbicidal effect and the degree of phytotoxicity were rated according to the following criterion.

The evaluation of the effect is expressed in the following rating 0 to 10 according to the weed killing rate relative to that in the non-treated area.

| Rating | Weed-kill ratio based on the control |
|---|---|
| 10: | 100% (withered) |
| 9: | at least 90% but less than 100% |
| 8: | at least 80% but less than 90% |
| 7: | at least 70% but less than 80% |
| 6: | at least 60% but less than 70% |
| 5: | at least 50% but less than 60% |
| 4: | at least 40% but less than 50% |
| 3: | at least 30% but less than 40% |
| 2: | at least 20% but less than 30% |
| 1: | at least 10% but less than 20% |
| 0: | less than 10% (not effective) |

The evaluation of phytotoxicity to paddy rice plants is expressed in the following rating 0 to 10 according to the phytotoxicity relative to that in the non-treated area.

| Rating | Phytotoxicity rate in comparison with the control |
|---|---|
| 10: | at least 90% (fatal damage) |
| 9: | at least 80% but less than 90% |
| 8: | at least 70% but less than 80% |
| 7: | at least 60% but less than 70% |
| 6: | at least 50% but less than 60% |
| 5: | at least 40% but less than 50% |
| 4: | at least 30% but less than 40% |
| 3: | at least 20% but less than 30% |
| 2: | at least 10% but less than 20% |
| 1: | more than 0 but less than 10% |
| 0: | 0% (no phytotoxicity) |

The results of the test are given in Table 1.

TABLE 1

| Compound No. | Dosage of active ingredient kg/ha | Herbicidal Effect Weeds | | | | | | | | Phytotoxicity Rice |
|---|---|---|---|---|---|---|---|---|---|---|
| | | A | B | C | D | E | F | G | H | |
| (1) | 0.2 | 10 | 10 | 10 | 10 | 10 | 10 | 10 | 10 | 0 |
| (2) | 0.2 | 10 | 10 | 10 | 10 | 10 | 10 | 10 | 10 | 0 |
| (3) | 0.2 | 10 | 10 | 10 | 10 | 10 | 10 | 10 | 10 | 0 |
| (5) | 0.2 | 10 | 10 | 10 | 10 | 10 | 10 | 10 | 10 | 0 |
| (16) | 0.2 | 10 | 10 | 10 | 10 | 10 | 10 | 10 | | 0 |
| (17) | 0.2 | 10 | 10 | 10 | 10 | 10 | 10 | 10 | | 0 |
| (18) | 0.2 | 10 | 10 | 10 | 10 | 10 | 10 | 10 | | ·0 |
| (20) | 0.2 | 10 | 10 | 10 | 10 | 10 | 10 | 10 | | 0 |
| (22) | 0.2 | 10 | 10 | 10 | 10 | 10 | 10 | 10 | | 0 |
| (23) | 0.2 | 10 | 10 | 10 | 10 | 10 | 10 | 10 | | 0 |
| Comparative V-1 | 0.2 | 10 | 9 | 10 | 10 | 10 | 10 | 5 | 10 | 9 |

Note:
The symbols A, B, C, D, E, F, G and H stand for the following weeds:
A: *Echinochloa crus-galli* Beauv. var.
B: *Eleocharia Acicularis* L.
C: *Cyperus iria* L.
D: *Scirpus juncoides* Roxburgh var.
E: *Monochoria vaginalis* Presl.
F: Broadleaf weeds (such as *Lindernia Procumbens* Philcox, *Rotala indica* Koehne and *Elatiae triandra* Schk.)
G: *Cyperus serotinus* Rottboel
H: *Sagittaria pygmaea* Miq.

Compounds (4), (6) to (15), (19), (21), (24), (25) and (26) were also confirmed to have excellent selective herbicidal activity without exhibiting any phytotoxicity to rice plants by tests similar to that above.

It is understood that the specification and examples are illustrative but not limitative of the present invention and that other embodiments within the spirit and scope of the invention will suggest themselves to those skilled in the art.

We claim:

1. A substituted phenylsulfonylurea derivative of the formula

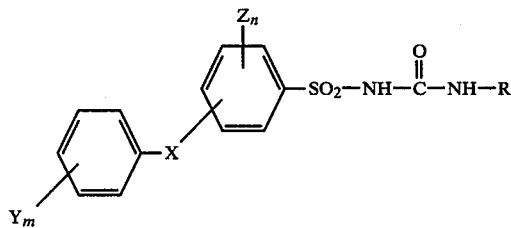

wherein
X is an oxygen atom or a direct bond,
Y and Z each independently is a halogen atom, a $C_1$ to $C_6$ alkyl group, a $C_1$ to $C_6$ alkoxy group or a nitro group,
R is

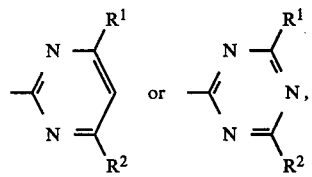

$R^1$ and $R^2$ each independently is a $C_1$ to $C_6$ alkyl group or a $C_1$ to $C_6$ alkoxy group,
m and n each independently is 0, 1 or 2, and
$m+n \neq 0$.

2. A Compound according to claim 1, in which Y and Z each independently is a fluorine, chlorine, bromine or iodine atom, or a methyl, ethyl, propyl, isopropyl, n-(iso-, sec- or tert.-) butyl, methoxy, ethoxy, propoxy, isopropoxy, n-(iso-, sec- or tert.-) butoxy or nitro group, and $R^1$ and $R^2$ each independently is methyl, ethyl, propyl, isopropyl, n-(iso-, sec- or tert.-) butyl, methoxy, ethoxy, propoxy, isopropoxy or n-(iso-, sec- or tert.-) butoxy.

3. A compound according to claim 1, wherein such compound is N-2-(2-chlorophenoxy)-phenylsulfonyl, N'-(4-methoxy-6-methyl-2-pyrimidyl) urea of the formula

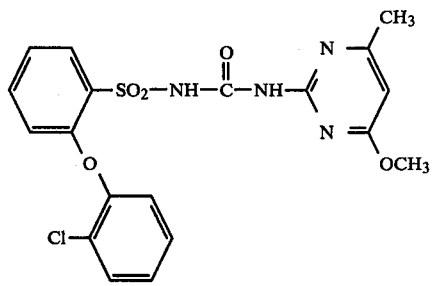

4. A herbicidal composition comprising a herbicidally effective amount of a compound according to claim 1 in admixture with a diluent.

5. A method of combating weeds comprising applying to the weeds, or to a habitat thereof, a herbicidally effective amount of a compound according to claim 1.

6. The method according to claim 5, wherein such compound is N-2-(2-chlorophenoxy)-phenylsulfonyl, N'-(4-methoxy-6-methyl-2-pyrimidyl) urea.

UNITED STATES PATENT AND TRADEMARK OFFICE
CERTIFICATE OF CORRECTION

PATENT NO. : 4,474,600  
DATED : October 2, 1984  
INVENTOR(S) : Masahiro Aya et al Page 1 of 2

It is certified that error appears in the above-identified patent and that said Letters Patent is hereby corrected as shown below:

| | |
|---|---|
| Abstract, lines 10 and 11, Col. 2, lines 41, 42 and 60, Col. 3, lines 12, 29, 63, 64, Col. 4, lines 25, and 27, Col. 6, line 26, Col. 21, line 37, Col. 22, line 1 | Delete "m and n" and substitute --$\underline{m}$ and $\underline{n}$-- |
| Col. 1, line 43 | Delete "n" and substitute --$\underline{n}$-- |
| Col. 1, line 58 | Delete "toms" and substitute --atoms-- |
| Col. 3, line 64 | After "not" insert --both-- |
| Col. 5, line 37 | After "methyl" delete "ether" and substitute --ethyl ether-- |
| Col. 5, line 42 | Delete "acetone" and substitute --acetate-- |
| Col. 8, line 41 | Correct spelling of "Monochoria" |
| Col. 14, Table 2, Compound No. 3, under column "R" | Delete formula and substitute 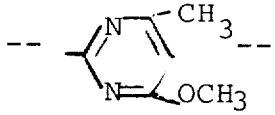 |
| Col. 14, Table 2, Compound No. 6 under column "R" | Delete formula and substitute 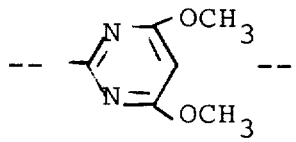 |
| Col. 15, Table 2, Compound Nos. 7, 10 and 13 under column "R" | Delete formula and substitute |

UNITED STATES PATENT AND TRADEMARK OFFICE
CERTIFICATE OF CORRECTION

PATENT NO. : 4,474,600

DATED : October 2, 1984

INVENTOR(S) : Masahiro Aya et al

It is certified that error appears in the above-identified patent and that said Letters Patent is hereby corrected as shown below:

| | |
|---|---|
| Col. 15, Table 2, Compound No. 9, under column "R" | Delete formula and substitute 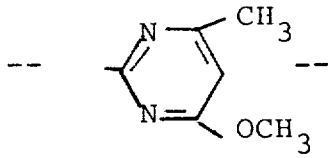 |
| Col. 18, Table 3, under "Product", Compounds No. 20, 23 and 24 | Delete "triazine" and substitute --triazin-- 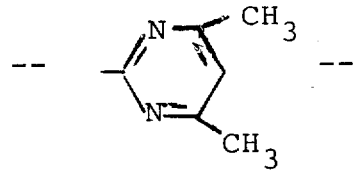 |

Signed and Sealed this

Seventh Day of May 1985

[SEAL]

Attest:

DONALD J. QUIGG

Attesting Officer

Acting Commissioner of Patents and Trademarks

REEXAMINATION CERTIFICATE (586th)
United States Patent [19]
Masahiro et al.

[11] B1 4,474,600
[45] Certificate Issued Nov. 4, 1986

[54] HERBICIDALLY ACTIVE NOVEL SUBSTITUTED PHENYLSULFONYLUREA DERIVATIVES

[75] Inventors: Aya Masahiro; Junichi Saito; Kazuomi Yasui, all of Tokyo; Kozo Shiokawa, Kanagawa; Norihisa Morishima, Tokyo; Toshio Goto, Kanagawa, all of Japan

[73] Assignee: Nihon Tokushu Noyaku Seizo K.K., Tokyo, Japan

Reexamination Request:
No. 90/000,953, Feb. 5, 1986

Reexamination Certificate for:
Patent No.: 4,474,600
Issued: Oct. 2, 1984
Appl. No.: 415,629
Filed: Sep. 7, 1982

[30] Foreign Application Priority Data

Sep. 16, 1981 [JP] Japan ................. 56-144590

[51] Int. Cl.[4] ............... A01N 43/54; A01N 43/66; C07D 239/42; C07D 251/16
[52] U.S. Cl. ........................... 71/92; 71/93; 544/194; 544/211; 544/320; 544/321; 544/328; 544/332; 564/90
[58] Field of Search ............... 544/332, 321, 211; 71/92, 93

[56] References Cited

U.S. PATENT DOCUMENTS 4,378,991  4/1983  Levitt ..................... 71/93

Primary Examiner—Catherine L. Mills

[57] ABSTRACT

Substituted phenylsulfonylurea-derivatives of the general formula

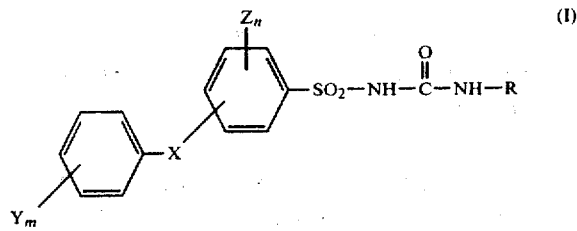

wherein X represents an oxygen atom or a direct bond, Y and Z each represents a halogen atom, a lower alkyl group, a lower alkoxy group or a nitro group, R represents a group:

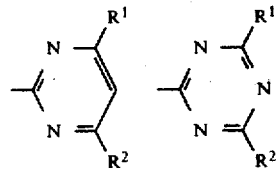

wherein $R^1$ and $R^2$ each represents a lower alkyl group or a lower alkoxy group, m and n each represents 0, 1 or 2 with the priviso that m and n do not represent 0 at the same time, are novel and find use as herbicides. Corresponding substituted benzenesulfonyl isocyanates are novel intermediate compounds for use in preparing compounds of formula (I).

REEXAMINATION CERTIFICATE ISSUED UNDER 35 U.S.C. 307

THE PATENT IS HEREBY AMENDED AS INDICATED BELOW.

Matter enclosed in heavy brackets [] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claims 2-6, dependent on an amended claim, is determined to be patentable.

1. A substituted phenylsulfonylurea derivative of the formula

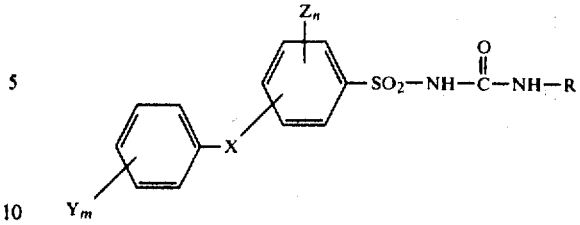

wherein
X is an oxygen atom [or a direct bond,]
Y and Z each independently is a halogen atom, a $C_1$ to $C_6$ alkyl group, a $C_1$ to $C_6$ alkoxy group or a nitro group,
R is

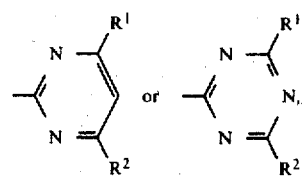

$R^1$ and $R^2$ each independently is a $C_1$ to $C_6$ alkyl group or a $C_1$ to $C_6$ alkoxy group,
m and n each independently is 0, 1 or 2, and $m+n \neq 0$.

* * * * *